US012751757B2

(12) United States Patent
Wootten

(10) Patent No.: US 12,751,757 B2
(45) Date of Patent: Oct. 6, 2026

(54) PLASMA FRACTIONATION DEVICE FOR SKIN REJUVENATION

(71) Applicant: Aesthetics Biomedical, Inc., Phoenix, AZ (US)

(72) Inventor: Shaun Wootten, Queen Creek, AZ (US)

(73) Assignee: Aesthetics Biomedical, Inc., Phoenix, AZ (US)

( * ) Notice: Subject to any disclaimer, the term of this patent is extended or adjusted under 35 U.S.C. 154(b) by 1140 days.

(21) Appl. No.: 17/704,415

(22) Filed: Mar. 25, 2022

(65) Prior Publication Data

US 2022/0304738 A1 Sep. 29, 2022

Related U.S. Application Data

(60) Provisional application No. 63/165,837, filed on Mar. 25, 2021.

(51) Int. Cl.

*A61B 18/18* (2006.01)
*A61B 18/04* (2006.01)
*A61B 18/00* (2006.01)

(52) U.S. Cl.

CPC .... *A61B 18/042* (2013.01); *A61B 2018/0047* (2013.01); *A61B 2018/00994* (2013.01)

(58) Field of Classification Search

CPC .............. A61B 18/042; A61B 18/1477; A61B 2018/0047; A61B 2018/00994
See application file for complete search history.

(56) References Cited

U.S. PATENT DOCUMENTS 6,099,523 A * 8/2000 Kim .................... A61B 18/1492 606/49
8,329,437 B1 * 12/2012 Ayliffe ............... G01N 15/1023 435/173.9
10,881,882 B1 1/2021 Schwarz et al.
2010/0100094 A1 * 4/2010 Truckai ................ A61B 18/042 606/39
2011/0028970 A1 2/2011 Woloszko et al.
2016/0181069 A1 6/2016 Watson et al.
2016/0331436 A1 * 11/2016 Holbeche ............. A61B 18/203
2017/0303381 A1 * 10/2017 Wang ........................ H05H 1/46
2017/0339776 A1 11/2017 Knoll et al.
2018/0214067 A1 * 8/2018 Filloux ................ A61B 18/042
2018/0263550 A1 * 9/2018 Filloux .............. A61B 18/1485
2020/0197077 A1 * 6/2020 Winkelman ....... A61B 18/1477
2020/0205277 A1 * 6/2020 Kim .................. H01J 37/32449
2021/0236193 A1 * 8/2021 Wootten ................. A61B 18/14
2025/0185357 A1 * 6/2025 Huang ............... H10D 84/0177

FOREIGN PATENT DOCUMENTS

WO 2019/238863 A1 12/2019
WO 2020/086552 A1 4/2020

* cited by examiner

*Primary Examiner* — Michael F Peffley
*Assistant Examiner* — Amanda L Zink
(74) *Attorney, Agent, or Firm* — Zeman-Mollen & Ford, LLP

(57) ABSTRACT

A plasma fractionation device having a removable cartridge connected to a handpiece where the removable cartridge includes a plurality of channels or magnetic poles that are filled with an inert gas that can be activated to produce plasma which exits the cartridge through the plurality of channels or magnetic poles. The plasma exiting through the plurality of channels or magnetic poles simultaneously creates a plurality of epidermal wounds.

22 Claims, 5 Drawing Sheets

PLASMA MICRONEEDLING

PLASMA FRACTIONATION DEVICE FOR SKIN REJUVENATION

CROSS-REFERENCE TO RELATED APPLICATIONS

This application claims priority to provisional patent application having Ser. No. 63/165,837 filed Mar. 25, 2021, which is herein incorporated by reference in its entirety.

FIELD OF INVENTION

The present invention is directed to a plasma fractionation device for skin rejuvenation which utilizes a cartridge having a plurality of channels or magnetic poles to direct plasma through a plurality of openings or nozzles at the end of the channels which enable multiple epidermal wounds to be created with one pulse. The cartridge itself may take the form of any number of geometries and the channels or magnetic poles contained within the cartridge may also take the form of any number of geometries either singularly, or in combination with one another, in order to treat specific areas of the skin.

BACKGROUND OF THE INVENTION

Plasma pens are known in the art and provide a popular non-invasive method for lifting, tightening, and rejuvenating the skin. Plasma pens harness the power of plasma by ionizing gases from the atmospheric air to create a micro-electrical discharge or ARC. Although the ARC never touches the skin, it causes a micro-injury to the skin's epidermal layer while simultaneously heating and disrupting the deeper dermal layer via thermal conductions. Plasma pens are used to improve skin texture and tone, reduce and remove wrinkles and scars, and treat aging skin that loses its elasticity. Plasma pens are also used to treat areas around the eyes to lift eyelids and remove bags under the eyes.

Plasma pens place epidermal wounds on the skin one at a time in approximately a 0.2 mm diameter circle. Using a single pulse of plasma to create a single epidermal wound can be a tedious process that takes a considerable amount of time to treat an area of the skin such as the areas of skin around the eyes and mouth. By fractionating the plasma in a plasma pen, a larger surface area of skin can be treated by stamping several wounds (approximately up to about 40 wounds) with one pulse. Accordingly, there is a need for a plasma pen capable of fractionating plasma in order to create multiple wounds at a time with one pulse so that a larger surface area of skin can be treated.

SUMMARY OF THE INVENTION

The present invention provides a plasma fractionation device that enables plasma treatment of a larger area of skin resulting in reduced treatment time. Power is optimized with utilizing plasma fractionation because less power is used when creating multiple epidermal wounds with one energy pulse. Due to the ability to treat larger surface areas, the whole body can be targeted for plasma skin rejuvenation.

The plasma fractionation device of the present invention includes a handpiece connected to a removable cartridge having a plurality of channels or magnetic poles that are filled with an ionizable gas that can be activated to produce plasma which exits the cartridge through the plurality of channels or magnetic poles. The plasma exiting through the plurality of channels or magnetic poles simultaneously creates a plurality of epidermal wounds. The removable cartridge may take the form of any number of geometric configurations and the plurality of channels or magnetic poles contained within the removable cartridge may also take the form of any number of geometric configurations. The plurality of channels or magnetic poles, when taken together, may have the same geometric configuration as the removable cartridge or they may have a completely different geometric configuration than the removable cartridge. For example, both the removable cartridge and the channels or magnetic poles contained within the cartridge may have a cylindrical shape with the ends of the removable cartridge and the ends of the channels taken together forming a circular shape. In contrast, the removable cartridge may have a cylindrical shape with ends having a circular shape while the channels within the cartridge taken together may have an elongated box like shape with their ends forming a square shape.

One main concept of the invention is to provide a plasma fractionation device having a removable and/or disposable cartridge attached to a housing where the cartridge in conjunction with the housing is capable of simultaneously creating multiple epidermal wounds with plasma using the same amount of energy to create one epidermal wound. The plasma fractionation device may also include microneedles so that the device is capable of providing radiofrequency microneedling in conjunction with applying plasma. The plasma fractionation device may also include an infrared camera and/or a device capable of measuring bioelectric impedance to assist in controlling the temperature of the plasma. The plasma fractionation device may also include an ultrasonic probe to evaluate skin damage when applying plasma utilizing the device.

In one exemplary embodiment, the plasma fractionation device of the present invention includes a handpiece having a proximal end and a distal end, at least one electrode contained within the proximal end of the handpiece, a removable cartridge connected to the proximal end of the handpiece where the removable cartridge includes a plurality of channels filled with an ionizable gas and each of the channels filled with the ionizable gas is in communication with the electrode(s), an electrical contact board that enables selective activation of the device, an electrical contact connecting the electrode(s) to the electrical contact board, and an electrical cord that connects the electrical contact board to an energy source. The plasma fractionation device may further include one or more selection buttons in communication with the electrical contact board for selectively activating the device to provide one or more of a pulsed plasma application, a continuous plasma application, and a sputtering plasma application. The plasma fractionation device may also include a locking mechanism on the proximal end of the handpiece which enables a leak proof seal between the handpiece and the removable cartridge when the removable cartridge is connected to the handpiece.

The removable cartridge of the plasma fractionation device, as well as the end of the removable cartridge not connected to the handpiece, may form any number of geometries. The plurality of channels contained within the removable cartridge may form a same geometry as, or different geometry than, the removable cartridge itself or the end of the removable cartridge not connected to the handpiece. The removable cartridge may be disposable and/or the removable cartridge may include a plurality of magnetic poles that are optimized to selectively induce plasma from the ionizable gas contained within the channels of the removable cartridge. The removable cartridge may be sterilized prior to use and/or the removable cartridge may be sealed until the device is activated by employing one or more selection buttons.

An electrical current or an electromagnetic energy can be selectively applied to the inert gas contained within the plurality of channels to induce and control the amount of plasma. The plasma produced may a hot plasma and/or a cold plasma and it may be selectively partially ionized or fully ionized. The device can apply plasma with or without touching the skin and the plasma can produce a pattern of epidermal wounding or fractionated damage or it can produce epidermal stimulation without epidermal wounding.

Another exemplary embodiment of the plasma fractionation device of the present invention includes a handpiece having a proximal end and a distal end, a hollow conductive tubular member contained within the handpiece, an ionizable gas supply for supplying an ionizable gas to the hollow conductive tubular member, a removable cartridge having a proximal end and a distal end where the distal end of the removable cartridge is connected to the proximal end of the handpiece and where the removable cartridge includes a plurality of conductive channels therein that are joined to one another to form a single conductive channel located near the distal end of the removable cartridge so that gas supplied through the hollow conductive tubular member is also supplied to the single conductive channel and the plurality of conductive channels contained within the removable cartridge, an electrical contact board that enables selective activation of the device, an electrical contact connecting the electrical contact board to the hollow conductive tubular member; and an electrical cord that connects the electrical contact board to an energy source.

DESCRIPTION OF EXEMPLARY EMBODIMENTS

Figure 1:
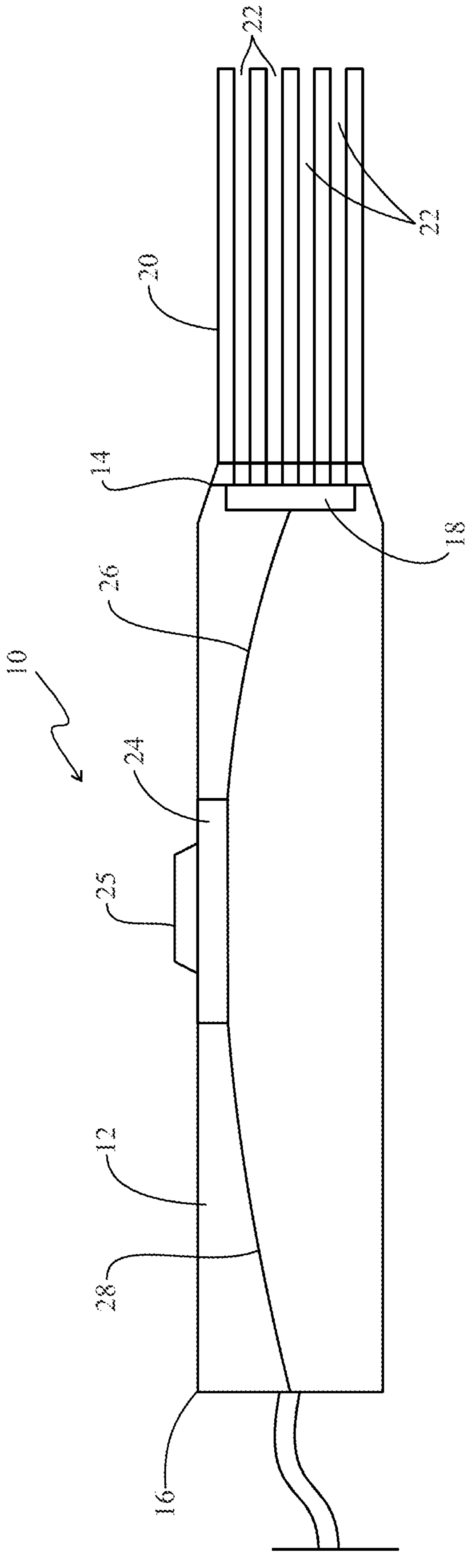
FIG. 1 is a cross-sectional view of one exemplary embodiment of the plasma fractionation device of the present invention.

The exemplary embodiments of the plasma fractionation device of the present invention enable a user to simultaneously create multiple epidermal wounds with plasma using the same amount of energy typically used to create one epidermal wound thereby enabling plasma treatment of large areas of a patient's skin while decreasing patient treatment time. The ability to treat a larger surface area of a patient's skin upon treatment allows for more body areas of a patient to be treated at a scheduled treatment time. In addition, the plasma fractionation device of the present invention may also include microneedles thereby enabling plasma treatment in conjunction with radiofrequency microneedling, thereby creating even more treatment options utilizing the device.

The plasma fractionation device of the present invention includes a handpiece or housing member that is capable of being connected to a removable cartridge. The removable cartridge includes a plurality of channels filled with, or capable of being filled with, an ionizable gas which is ionized by activation of the handpiece to produce plasma. The removable cartridges may be disposable and can be easily disconnected after use.

The identity of the elements/features that relate to the numbers shown in the drawing figures are as follows:

10 plasma fractionation device
12 handpiece
14 proximal end (of handpiece 12)
16 distal end (of handpiece 12)

18 at least one electrode
20 removable cartridge
22 plurality of channels/magnetic poles
24 electrical contact board
25 activation button(s)
26 electrical contact
28 electrical cord
40 plasma fractionation device
42 handpiece
44 proximal end (of handpiece 42)
46 distal end (of handpiece 42)
48 hollow conductive tubular member
50 ionizable gas supply
52 removable cartridge
54 proximal end (of cartridge 52)
56 distal end (of cartridge 52)
58 plurality of conductive channels
60 single conductive channel
62 electrical contact board
65 activation button(s)
64 electrical contact
66 electrical cord
68 circular proximal end of removable cartridge
70 ends of plurality of channels contained within cartridge 68
72 triangular proximal end of removable cartridge
74 ends of plurality of channels contained within cartridge 72
76 square proximal end of circular cartridge
78 ends of plurality of channels contained within cartridge 76
80 circular proximal end of removable cartridge with triangle cut out
82 ends of plurality of channels contained in cartridge 80
90 curved half-moon shaped proximal end of removable cartridge
92 ends of plurality of channels contained in cartridge 90
94 curved quarter-moon shaped proximal end of removable cartridge
96 ends of plurality of channels contained in cartridge 94
98 circular shaped proximal end of removable cartridge
100 round ends of plurality of hollow cylindrical shaped channels contained in cartridge
102 square ends of plurality of hollow rectangular shaped channels contained in cartridge 98
111 solid microneedles
112 hollow microneedles
114 openings
120 removable cartridge
122 microneedles
124 ionizable gas or plasma inlet
126 one or more electrodes
130 microneedle
132 attachment mechanism/member
134 support member
136 openings FIG. 1 is a cross-sectional view showing one exemplary embodiment of the plasma fractionation device 10 of the present invention. Plasma fractionation device 10 includes a handpiece 12 having a proximal end 14 and a distal end 16, and removable cartridge 20 connected to handpiece 12 wherein the removable cartridge 20 includes a plurality of channels 22 or magnetic poles that are prefilled with an ionizable gas. The channels 22 or magnetic poles are hollow conductive channels or hollow conductive magnetic poles that are capable of energizing an inert gas contained within the channels into plasma. The magnetic poles may be placed adjacent to a conductive channel. An electrode 18 is contained within the proximal end 14 of handpiece 12 and electrode 18 is in communication with prefilled channels 22. Handpiece 12 also includes an electrical contact board 24 that enables selective activation of the device 10 by pressing activation button(s) 25, an electrical contact 26, such as wire, for example, that connects the electrode 18 to the electrical contact board 24, and an electrical cord 28 that connects the electrical contact board 24 to an energy source, such as an electrical outlet, for example.

In order to use the plasma fractionation device 10, the cartridge 20 is connected to handpiece 12. Prior to connection to handpiece 12, the end of the cartridge 20 that is attached to handpiece 12 is sealed. Upon connection to the handpiece 12, the seal on cartridge 20 breaks. When a user presses activation button(s) 25, electrical energy activates electrode 18 which in turn ionizes the ionizable gas contained in the prefilled channels 22 within the cartridge 20 which in turn produces plasma for treatment. One or more activation buttons 25 may provide for a pulsed plasma application, a continuous plasma application, and/or a sputtering plasma application. A sputtering plasma application could be advantageous and provide a more uniform fractionation due to a reduced amount of time for the energy to arc and stray from its intended path. Energy travels to the path of least resistance and a sputtering plasma application may also result in less pain for the patient due to the lack of energy concentrating in one place. In addition to utilizing an electrical current to activate the device 10, the device 10 may also be activated using an electromagnetic energy including, but not limited to, radio waves, microwaves, sound waves, infrared, ultraviolet, and x-rays. The plasma fractionation device 10 may also include a plurality of magnetic poles contained within the handpiece 12 or the removable cartridge 20 where the magnetic poles are optimized to selectively induce plasma from the ionizable gas contained within the channels 22. The plasma fractionation device 10 may also include a locking mechanism on the proximal end of the handpiece 12 that enables a leak proof seal between the handpiece 12 and the removable cartridge 20 when the removable cartridge 20 is connected to the handpiece 12. Once the device 10 is activated, the seal may be partially broken to enable electrode 18 in handpiece 12 to activate the ionizable gas contained in the channels 22. The plasma fractionation device 10 may further include an infrared camera and/or a device capable of measuring bioelectrical impedance to assist in controlling the temperature of the plasma. In some instances, the bioimpedance could also be determined through the microneedles. In addition, the plasma fractionation device 10 may include an ultrasonic probe to evaluate skin damage when applying plasma utilizing the device.

Figure 9:
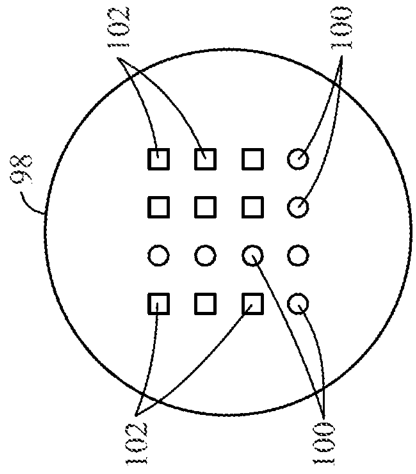
FIG. 9 is an end view of the removable cartridge of the plasma fractionation device where the end of the cartridge has a circular shape, the plurality of channels contained within the cartridge have a square shape, and the individual plurality of channels have two different shapes—hollow rectangular rods with square shaped ends and hollow cylindrical rods with circular shaped ends.

The removable cartridge 20 in the plasma fractionation device 10 may be sterilized before use and disposable after use. The end of the removable cartridge 20 that is not connected to the handpiece 12 (i.e. the proximal end of the removable cartridge 20) may comprise any number of geometries, some examples of which are shown in FIGS. 3A-3C, 4A-4C, 5A-5C, 6A-6B, 7-9. The plurality of channels 22 contained within the removable cartridge 20, taken together, may form a same geometry as the geometry of the removable cartridge 20, some examples of which are shown in FIGS. 3A, 4B, 4C, 5C, 6A-6B, and 7-8. Alternatively, the plurality of channels 22 contained within the removable cartridge 20, taken together, may form a different geometry than the geometry of the removable cartridge 20, some examples of which are shown in FIGS. 3B, 3C, 4A, 5A, 5B, and 9. In addition, the geometry of the individual channels 22 contained in the removable cartridge 20 may be different form one another as shown in FIG. 9. The removable cartridge 20 of the plasma fractionation device 10 may also include a plurality of microneedles to enable the device 10 to provide radiofrequency microneedling in conjunction with applying plasma. (See FIGS. 10-13). This enables the plasma to enter into the epidermis, dermis, and subcutaneous adipose tissue.

The plasma fractionation device 10 of the present invention may produce plasma that is hot and/or cold. The plasma fractionation device 10 of the present invention may produce plasma that is selectively partially ionized or fully ionized. The plasma fractionation device 10 of the present invention may provide plasma that produces a pattern of epidermal wounding or fractionated damage. The plasma fractionation device 10 of the present invention may provide plasma that produces epidermal stimulation without epidermal wounding. The plasma fractionation device 10 of the present invention may apply plasma with or without touching the skin.

Figure 2:
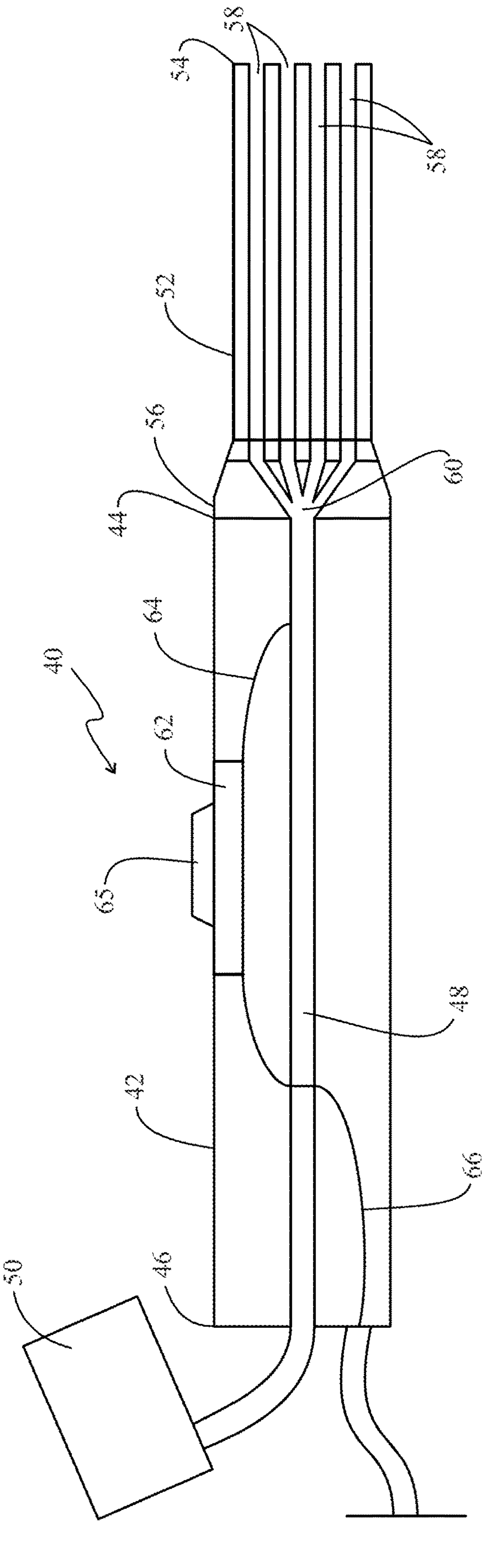
FIG. 2 is a cross-sectional view of another exemplary embodiment of the plasma fractionation device of the present invention.

FIG. 2 is a cross-sectional view showing another exemplary embodiment of the plasma fractionation device 40 of the present invention. Plasma fractionation device 10 includes a handpiece 42 having a proximal end 44 and a distal end 46, a hollow conductive tubular member 48 contained within the handpiece 42, an ionizable gas supply for supplying an ionizable gas to the hollow conductive tubular member 48, a removable cartridge 52 having a proximal end 54 and a distal end 56 wherein the distal end 56 of the removable cartridge 52 is connected to the proximal end 44 of the handpiece 42 and wherein the removable cartridge 52 includes a plurality of conductive channels 58 therein that are joined to one another to form a single conductive channel 60 located near the distal end 56 of the removable cartridge 52 so that gas supplied through the hollow conductive tubular member 48 is also supplied to the single conductive channel 60 and the plurality of conductive channels 58 contained within the removable cartridge 52, an electrical contact board 62 that enables selective activation of the device 40 by pressing activation button(s) 65, an electrical contact 64 connecting the electrical contact board 62 to the hollow conductive tubular member 48 and an electrical cord 66 that connects the electrical contact board 62 to an energy source. In this exemplary embodiment of the plasma fractionation device 40, an ionizable gas is supplied to the removable cartridge 52 by hollow conductive tubular member 48 that is contained within the handpiece 42. When a user presses activation button(s) 65, an ionizable gas is supplied from an ionizable gas supply 50 to hollow conductive tubular member 48 contained within handpiece 42, to single conductive channel 60 contained within removable cartridge 52, to the plurality of conductive channels 58 contained within removable cartridge 52. At the same time, electrical energy activates electrical contact 64 which in turn ionizes the ionizable gas contained in hollow conductive tubular member 48 which in turn produces plasma for treatment which is directed into single conductive channel 60 contained within removable cartridge 52 to the plurality of conductive channels 58 contained within removable cartridge 52. One or more activation buttons 65 may provide for a pulsed plasma application, a continuous plasma application, and/or a sputtering plasma application. In another exemplary embodiment, there may be no single conductive channel 60 in the removable cartridge 52 that connects to the plurality of conductive channels 58 in the removable cartridge 52. Instead, the diameter of the hollow conductive tubular member 48 in the handpiece 42 may be wide enough to extend across all of the diameters of the plurality of conductive channels 58 contained in the removable cartridge 52 when the removable cartridge 52 is connected to the handpiece 42 and locked into place. There may be a locking mechanism that secures the removable cartridge 52 to the handpiece 42 when they are connected to one another.

The plasma fractionation device 40 shown in FIG. 2 may also include many of the features described above with respect to the plasma fractionation device 10 shown in FIG. 1. For example, the plasma fractionation device 40 may also include a plurality of magnetic poles contained within the handpiece 42 or the removable cartridge 52 where the magnetic poles are optimized to selectively induce plasma from the ionizable gas contained within the channels 58. The plasma fractionation device 40 may further include an infrared camera and/or a device capable of measuring bioelectrical impedance to assist in controlling the temperature of the plasma. In addition, the plasma fractionation device 40 may include an ultrasonic probe to evaluate skin damage when applying plasma utilizing the device. The removable cartridge 52 in the plasma fractionation device 40 may be sterilized before use and disposable after use.

Like the proximal end of the removable cartridge 20 in plasma fractionation device 10, the proximal end 54 of the removable cartridge 52 in plasma fractionation device 40 may comprise any number of geometries, some examples of which are shown in FIGS. 3A-3C, 4A-4C, 5A-5C, 6A-6B, 7-9. The plurality of channels 58 contained within the removable cartridge 52, taken together, may form a same geometry as the geometry of the removable cartridge 52, some examples of which are shown in FIGS. 3A, 4B, 4C, 5C, 6A-6B, and 7-8. Alternatively, the plurality of channels 58 contained within the removable cartridge 52, taken together, may form a different geometry than the geometry of the removable cartridge 52, some examples of which are shown in FIGS. 3B, 3C, 4A, 5A, 5B, and 9. In addition, the geometry of the individual channels 58 contained in the removable cartridge 52 may be different form one another as shown in FIG. 9. The removable cartridge 52 of the plasma fractionation device 40 may also include a plurality of microneedles to enable the device 40 to provide radiofrequency microneedling in conjunction with applying plasma. (See FIGS. 10-13)

Figure 3A:
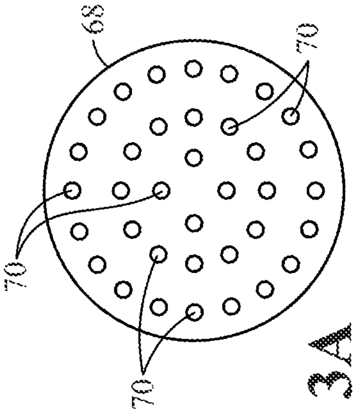
FIGS. 3A-3C are end views of the removable cartridge of the plasma fractionation device where the end of the cartridge has a circular shape and the plurality of channels contained within the cartridge together form varying geometric shapes.
Figure 3B:
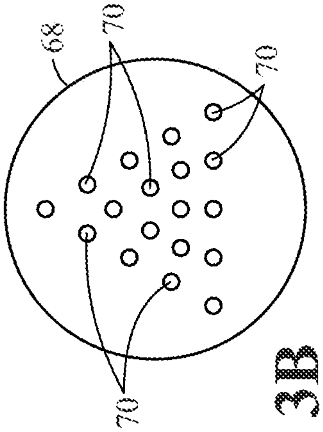
Figure 3C:
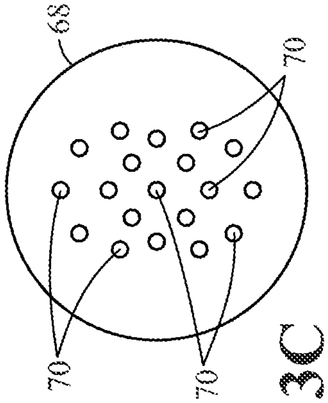
Figure 4A:
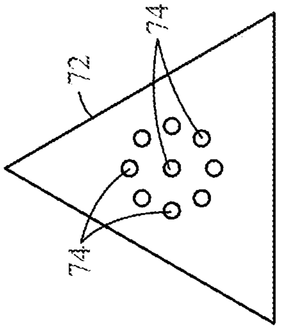
FIGS. 4A-4C are end views of the removable cartridge of the plasma fractionation device where the end of the cartridge has a triangular shape and the plurality of channels contained within the cartridge together form varying geometric shapes.
Figure 4B:
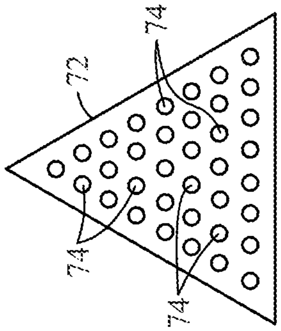
Figure 4C:
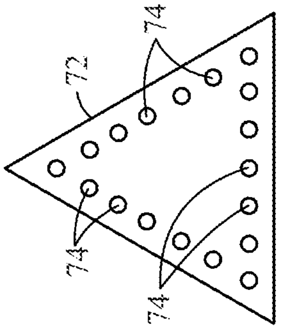
Figure 5A:
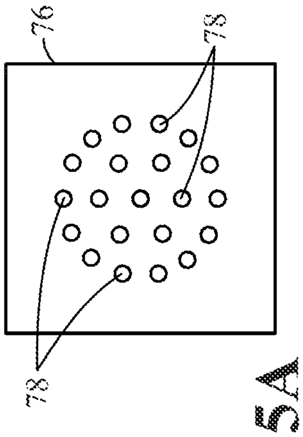
FIGS. 5A-5C are end views of the removable cartridge of the plasma fractionation device where the end of the cartridge has a square shape and the plurality of channels contained within the cartridge together form varying geometric shapes.
Figure 5B:
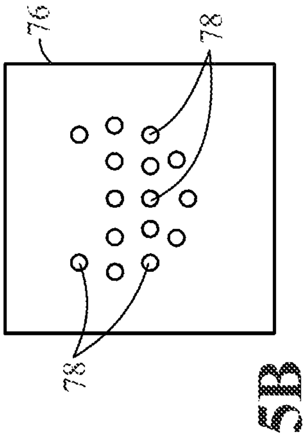
Figure 5C:
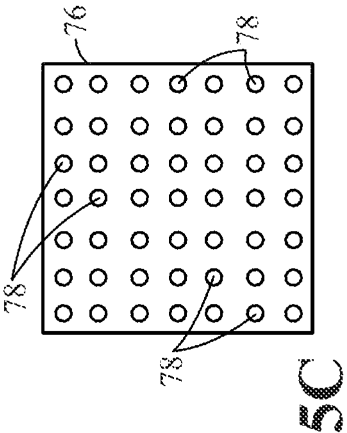
Figure 6A:
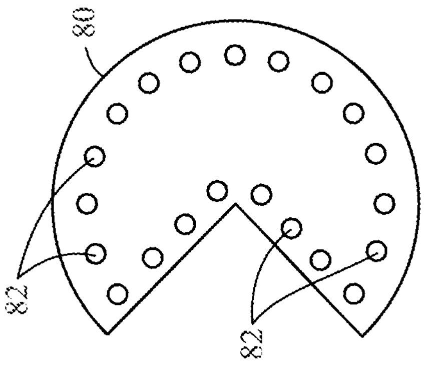
FIGS. 6A-6B are end views of the removable cartridge of the plasma fractionation device where the end of the cartridge has a circular shape with a triangle cut out and the plurality of channels contained within the cartridge together form varying geometric shapes.
Figure 6B:
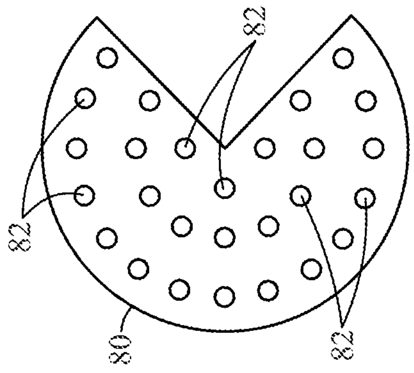

FIGS. 3A-3C are end views of the removable cartridge of the plasma fractionation device where the end of the cartridge has a circular shape and the plurality of channels contained within the cartridge together form varying geometric shapes—a circular shape in FIG. 3A, a triangular shape in FIG. 3B, and an generally undefined vertical oblong shape in FIG. 3C. FIGS. 4A-4C are end views of the removable cartridge of the plasma fractionation device where the end of the cartridge has a triangular shape and the plurality of channels contained within the cartridge together form varying geometric shapes—a circular shape in FIG. 4A, a solid triangular shape in FIG. 4B, and a hollow triangular shape in FIG. 4C. FIGS. 5A-5C are end views of the removable cartridge of the plasma fractionation device where the end of the cartridge has a square shape and the plurality of channels contained within the cartridge together form varying geometric shapes—a circular shape in FIG. 5A, a half-moon shape in FIG. 5B, and a square shape in FIG. 5C. FIGS. 6A-6C are end views of the removable cartridge of the plasma fractionation device where the end of the cartridge has a circular shape with a triangle cut out and the plurality of channels contained within the cartridge together form varying geometric shapes—a hollow circular shape with a triangle cut out in FIG. 6A, and a solid circular shape with a triangle cut out in FIG. 6B.

Figure 7:
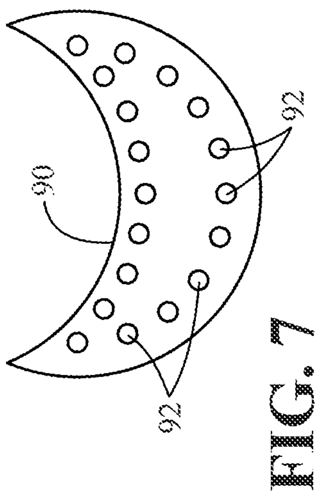
FIG. 7 is an end view of the removable cartridge of the plasma fractionation device where the end of the cartridge has a curved half-moon like shape and the plurality of channels are formed about the circumference of the curved half-moon like shape of the cartridge.
Figure 8:
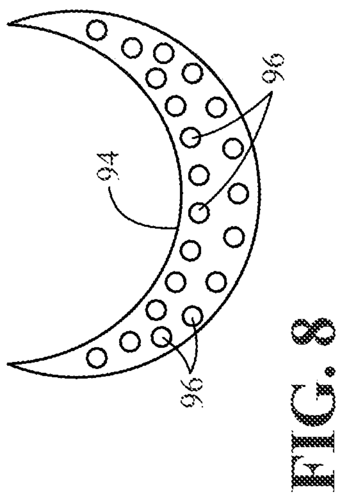
FIG. 8 is an end view of the removable cartridge of the plasma fractionation device where the end of the cartridge has a curved quarter-moon like shape and the plurality of channels are formed about the circumference of the curved half-moon like shape of the cartridge.

FIG. 7 is an end view of the removable cartridge of the plasma fractionation device where the end of the cartridge has a curved half-moon like shape and the plurality of channels are formed about the circumference of the curved half-moon like shape of the cartridge. FIG. 8 is an end view of the removable cartridge of the plasma fractionation device where the end of the cartridge has a curved quarter-moon like shape and the plurality of channels are formed about the circumference of the curved half-moon like shape of the cartridge. FIG. 9 is an end view of the removable cartridge of the plasma fractionation device where the end of the cartridge has a circular shape, the plurality of channels contained within the cartridge have a square shape, and the individual plurality of channels have two different shapes—hollow rectangular rods with square shaped ends and hollow cylindrical rods with circular shaped ends.

Figure 10:
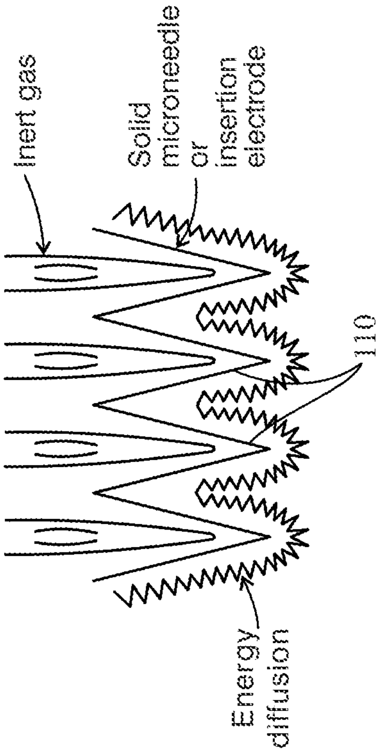
FIG. 10 is a schematic showing a side cross-sectional view of an exemplary configuration of, and application of energy to, a plurality of microneedles which may be contained within the removable cartridge of the plasma fractionation device of the present invention to enable plasma microneedling.

FIG. 10 is a schematic showing a side cross-sectional view of an exemplary configuration of, and application of energy to, a plurality of microneedles 110 which may be contained within the removable cartridge of the plasma fractionation device of the present invention to enable plasma microneedling. As shown in FIG. 10, a plurality of solid microneedles 110 or insertion electrodes are contained within the removable cartridge of any of the exemplary embodiments of the plasma fractionation device. An ionized gas comes into contact with the solid microneedles 110 and energy is diffused around the tips of the microneedles 110 as shown. Microneedling is performed simultaneously with plasma treatment.

Figure 11:
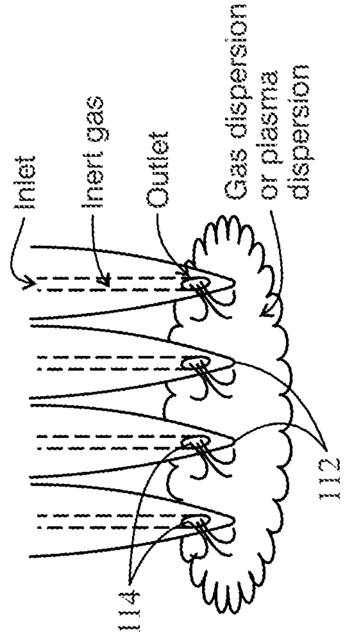
FIG. 11 is a schematic showing a side cross-sectional view of an exemplary configuration of, and application of energy to, a plurality of hollow microneedles having openings in or near their sharp tips which may be contained within the removable cartridge of the plasma fractionation device of the present invention to enable plasma microneedling.

FIG. 11 is a schematic showing a side cross-sectional view of an exemplary configuration of, and application of energy to, a plurality of hollow microneedles 112 having openings in or near their sharp tips which may be contained within the removable cartridge of the plasma fractionation device of the present invention to enable plasma microneedling. As shown in FIG. 11, a plurality of hollow microneedles 112 each having an opening 114 in or near their sharp tip are contained within the removable cartridge of any of the exemplary embodiments of the plasma fractionation device. An ionized gas travels into the hollow microneedles 112 and exits through openings 114 near their sharp tips. Ionized gas is dispersed through and around the tips of the microneedles 112 as shown. Microneedling is performed simultaneously with plasma treatment.

Figure 12:
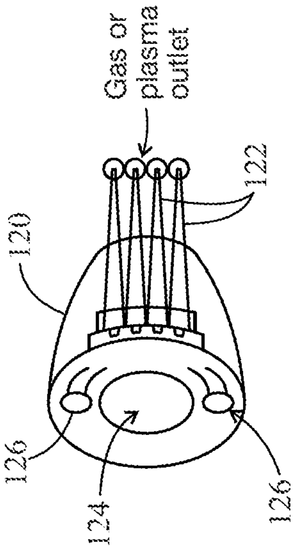
FIG. 12 is an exemplary embodiment of a removable cartridge included in the plasma fractionation device of the present invention wherein the removable cartridge includes a plurality of microneedles to enable plasma microneedling.

FIG. 12 is an exemplary embodiment of a removable cartridge 120 included in the plasma fractionation device of the present invention wherein the removable cartridge 120 includes a plurality of microneedles 122 to enable plasma microneedling. Removable cartridge 120 also includes an ionizable gas or plasma inlet 124 that is in communication with the microneedles 122 and one or more electrodes 126 for transferring current to the microneedles 122. Microneedling is performed simultaneously with plasma treatment utilizing this removable cartridge 120.

Figure 13:
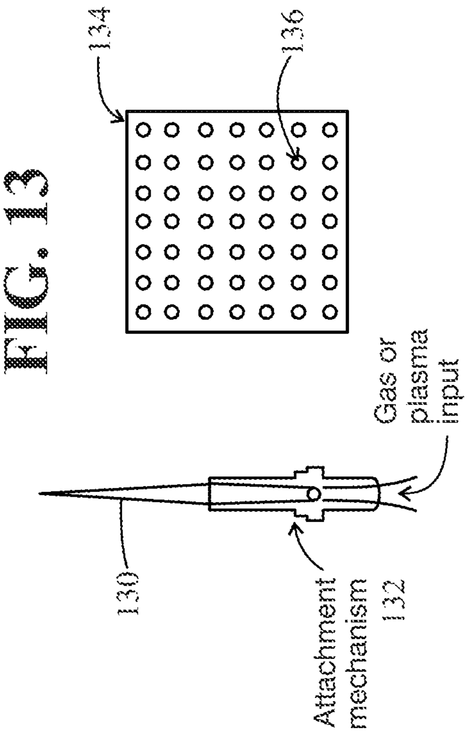
FIG. 13 shows an exemplary embodiment of a microneedle connected to an attachment mechanism/member which in turn can be connected to a support member, all of which are contained within a removable cartridge of the plasma fractionation device of the present invention.

FIG. 13 shows an exemplary embodiment of a microneedle 130 connected to an attachment mechanism/member 132 which in turn can be connected to a support member 134, all of which are contained within a removable cartridge of the plasma fractionation device of the present invention. An ionizable gas or plasma is directed into the attachment mechanism/member 132 which in turn is directed into the microneedle 130. Support member 134 may be a printed circuit board, in some instances, with openings 136 therein into which the attachment mechanism/member 132 can be inserted The drawings and description of exemplary embodiments of the invention herein shows various exemplary embodiments of the invention. These exemplary embodiments and modes are identified in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. A plasma fractionation device comprising:

a handpiece having a proximal end and a distal end;

at least one electrode contained within the proximal end of the handpiece;

a removable cartridge connected to the proximal end of the handpiece that is sealed until activation of the device wherein the removable cartridge includes a plurality of channels filled with an ionizable gas and each of the channels filled with an ionizable gas is in communication with said at least one electrode;

an electrical contact board that enables selective activation of the device by selecting one or more selection buttons in communication with the electrical board;

an electrical contact connecting said at least one electrode to the electrical contact board; and an electrical cord that connects the electrical contact board to an energy source.

2. The plasma fractionation device of claim 1 wherein an end of the removable cartridge not connected to the handpiece may comprise any number of geometries.

3. The plasma fractionation device of claim 2 wherein the plurality of channels contained within the removable cartridge together form a same geometry as the removable cartridge.

4. The plasma fractionation device of claim 2 wherein the plurality of channels contained within the removable cartridge together form a different geometry than the geometry of the removable cartridge.

5. The plasma fractionation device of claim 1 further comprising a plurality of magnetic poles contained within the handpiece or the removable cartridge wherein the plurality of magnetic poles are optimized to selectively induce plasma from the ionizable gas contained within the channels of the removable cartridge.

6. The plasma fractionation device of claim 1 wherein the one or more selection buttons in communication with the electrical contact board provide for one or more of a pulsed plasma application, a continuous plasma application, and a sputtering plasma application.

7. The plasma fractionation device of claim 1 further comprising a locking mechanism on the proximal end of the handpiece which enables a leak proof seal between the handpiece and the removable cartridge when the removable cartridge is connected to the handpiece.

8. The plasma fractionation device of claim 1 wherein at least one of an electrical current and an electromagnetic energy can be selectively applied to the ionizable gas contained within the plurality of channels to induce and control the amount of plasma.

9. The plasma fractionation device of claim 1 wherein the removable cartridge further includes microneedles and the device is capable of providing radiofrequency microneedling in conjunction with applying plasma.

10. The plasma fractionation device of claim 1 wherein the device further includes at least one of an infrared camera and a device capable of measuring bioelectric impedance to assist in controlling the temperature of the plasma.

11. The plasma fractionation device of claim 1 wherein the device further includes an ultrasonic probe to evaluate skin damage when applying plasma utilizing the device.

12. A plasma fractionation device comprising:

a handpiece having a proximal end and a distal end;

a hollow conductive tubular member contained within the handpiece;

an ionizable gas supply for supplying an ionizable gas to the hollow conductive tubular member;

a removable cartridge having a proximal end and a distal end that is sealed until activation of the device wherein the distal end of the removable cartridge is connected to the proximal end of the handpiece and wherein the removable cartridge includes a plurality of conductive channels therein that are joined to one another to form a single conductive channel located near the distal end of the removable cartridge so that gas supplied through the hollow conductive tubular member is also supplied to the single conductive channel and the plurality of conductive channels contained within the removable cartridge;

an electrical contact board that enables selective activation of the device by selecting one or more selection buttons in communication with the electrical contact board;

an electrical contact connecting the electrical contact board to the hollow conductive tubular member; and an electrical cord that connects the electrical contact board to an energy source.

13. The plasma fractionation device of claim 12 wherein the plurality of conductive channels contained within the removable cartridge together form a different geometry than a geometry of the proximal end of the removable cartridge.

14. The plasma fractionation device of claim 12 wherein the removable cartridge includes a plurality of magnetic poles that are optimized to selectively induce plasma from an ionizable gas supplied to the plurality of conductive channels contained within the removable cartridge.

15. The plasma fractionation device of claim 12 wherein the one or more selection buttons in communication with the electrical contact board provide for one or more of a pulsed plasma application, a continuous plasma application, and a sputtering plasma application.

16. The plasma fractionation device of claim 12 wherein at least one of an electrical current and an electromagnetic energy can be selectively applied to the ionizable gas contained within the plurality of conductive channels to induce and control the amount of plasma.

17. The plasma fractionation device of claim 12 wherein the removable cartridge further includes microneedles and the device is capable of providing radiofrequency microneedling in conjunction with applying plasma.

18. The plasma fractionation device of claim 12 wherein the device further includes at least one of an infrared camera and a device capable of measuring bioelectric impedance to assist in controlling the temperature of the plasma.

19. The plasma fractionation device of claim 12 wherein the device further includes an ultrasonic probe to evaluate skin damage when applying plasma utilizing the device.

20. The plasma fractionation device of claim 12 wherein the device further includes ultrasonic elements that produce acoustic waves and/or ultrasonic pressure in combination with plasma produced by the device.

21. A plasma fractionation device comprising:

a handpiece having a proximal end and a distal end;

at least one electrode contained within the proximal end of the handpiece;

a removable cartridge connected to the proximal end of the handpiece wherein the removable cartridge includes a plurality of channels filled with an ionizable gas and each of the channels filled with an ionizable gas is in communication with said at least one electrode;

an electrical contact board that enables selective activation of the device;

an electrical contact connecting said at least one electrode to the electrical contact board;

a plurality of magnetic poles contained within the handpiece or the removable cartridge wherein the plurality of magnetic poles are optimized to selectively induce plasma from the ionizable gas contained within the channels of the removable cartridge; and an electrical cord that connects the electrical contact board to an energy source.

22. The plasma fractionation device of claim 21 wherein the removable cartridge further includes microneedles and the device is capable of providing radiofrequency microneedling in conjunction with applying plasma.

* * * * *